US008735784B2

(12) United States Patent
Tabuse

(10) Patent No.: US 8,735,784 B2
(45) Date of Patent: May 27, 2014

(54) MICROWAVE INDUCTION HEATING DEVICE

(75) Inventor: Katsuyoshi Tabuse, Wakayama (JP)

(73) Assignee: Sunny Engineering Co., Ltd. (JP)

( * ) Notice: Subject to any disclaimer, the term of this patent is extended or adjusted under 35 U.S.C. 154(b) by 1165 days.

(21) Appl. No.: 12/353,618

(22) Filed: Jan. 14, 2009

(65) Prior Publication Data

US 2009/0212046 A1 Aug. 27, 2009

Related U.S. Application Data

(63) Continuation of application No. PCT/JP2007/063998, filed on Jul. 13, 2007.

(30) Foreign Application Priority Data

Jul. 14, 2006 (JP) ................................ 2006-193968

(51) Int. Cl.
*H05B 6/66* (2006.01)
*A61B 18/04* (2006.01)

(52) U.S. Cl.
USPC ................................ 219/702; 606/32; 606/33

(58) Field of Classification Search
CPC ............. H05B 6/666; H05B 6/80; H05B 6/68
USPC ......... 219/702, 700, 709, 679, 690, 695, 697, 219/746, 748, 750, 701; 606/7, 10–14, 15, 606/41, 309; 422/21; 204/157.15, 157.43; 264/432; 34/259; 607/101
See application file for complete search history.

(56) References Cited

U.S. PATENT DOCUMENTS 6,403,939 B1 6/2002 Fagrell
6,461,351 B1 * 10/2002 Woodruff et al. ............... 606/32
6,720,540 B2 4/2004 Fagrell
6,740,108 B1 * 5/2004 Just et al. ........................ 607/96
2007/0060990 A1 * 3/2007 Satake .......................... 607/101
2007/0299488 A1 * 12/2007 Carr .............................. 607/101
2011/0264085 A1 * 10/2011 Satake ............................ 606/33

FOREIGN PATENT DOCUMENTS

JP 08-187297 7/1996
JP 2002-246167 8/2002

* cited by examiner

*Primary Examiner* — Quang Van
(74) *Attorney, Agent, or Firm* — St. Onge Steward Johnston & Reens LLC

(57) ABSTRACT

A microwave induction heating device includes microwave oscillation means (100) for oscillating a microwave so that an object is heated by the induction heating of the microwave oscillated from the microwave oscillation means (100). The microwave oscillation means (100) is configured in such a manner that the frequency of the microwave oscillated from the microwave oscillation means (100) can be changed.

10 Claims, 7 Drawing Sheets

MICROWAVE INDUCTION HEATING DEVICE

CROSS-REFERENCE TO RELATED APPLICATIONS

This application is a continuation of application No. PCT/JP2007/063998, filed Jul. 13, 2007.

TECHNICAL FIELD

The invention of the subject application is the invention suitable for a microwave induction heating device, in particular, a medical appliance such as a microwave surgical device.

BACKGROUND OF THE INVENTION

Conventionally, well known among microwave surgical devices of this type are those which are equipped with a magnetron (microwave oscillation unit) for generating a microwave and an electrode for irradiating a treatment site being a portion to be heated, with the microwave generated in the magnetron, in a contact state. In such a microwave surgical device, the electrode is set in a contact state with a carcinoma tissue of a patient's liver, for example, and in this state, the microwave is oscillated and irradiated, thereby heating the carcinoma tissue so as to coagulate the tissue.

Herein, the microwave generating unit is that which generates a microwave of a fixed frequency, i.e., 2450 MHz.

In the microwave surgical devices, when progress of a heating process in a treatment site is slow, output of the microwave in the magnetron is increased. Even so, there is a case that a sufficient effect cannot be obtained even if the output is increased. On the other hand, when the treatment site is excessively heated, the treatment site is blackened, and in some cases, even carbonization occurs. As a result, the diseased site may be adversely affected.

Further, the magnetron is that which amplifies and uses the frequency of a certain value or more of an alternate power source. The microwave by the magnetron becomes intermittent output in which a cyclically output 0 state is present in relation to the cycle of the alternate power source (output that is not continuous in time) (see FIG. 8). Thus, there is a problem in that effective heating is not possible. FIG. 8 shows a measurement result of output waveforms of the microwave.

SUMMARY OF INVENTION

Therefore, the invention of the subject application has been devised in view of the aforementioned circumstances, and an object of the invention of the subject application is to provide a microwave induction heating device capable of precisely heating a portion to be heated.

In order to solve the aforementioned problems, a microwave induction heating device according to the invention of the subject application is a microwave induction heating device including microwave oscillation means for oscillating a microwave, and also heating an object by microwave induction heating oscillated from the microwave oscillation means, the microwave oscillation means adopts a configuration so that a frequency of the microwave oscillated by the microwave oscillation means can be changed.

In the invention of the subject application made of the configuration, the frequency of the microwave with which the object being a portion to be heated is irradiated can be changed according to the types of objects, states of objects, etc. Thus, the object to be heated can be precisely heated.

It is noted that in the invention of the subject application, the microwave oscillation means can be arranged to change the frequency of the oscillated microwave stepwise (e.g., three steps). However, the microwave oscillation means is preferably arranged so that it can be changed substantially continuously. In doing so, the portion to be heated can be heated more precisely. It is noted that "can be changed substantially continuously" includes to change the frequency continuously for each 1 MHz, for example.

The aforementioned configuration can be achieved by adopting a configuration such that the microwave oscillation means includes a microwave generation unit for generating a microwave and a microwave amplifying unit for amplifying the microwave generated in the microwave generation unit, and the microwave generation unit is arranged so that a frequency of the microwave to be generated can be changed substantially continuously. It is noted that when such a configuration is adopted, the microwave oscillation means can be arranged to irradiate a heating portion with a microwave continuous in time.

In the microwave induction heating device according to the invention of the subject application, it is preferable to adopt a configuration such that the microwave oscillated by the microwave oscillation means is arranged so as to receive a reflected wave reflected on the object being a portion to be heated. Thereby, based on the reflected wave thus received, the microwave oscillated from the microwave oscillation means can be changed, and according to the Voltage Standing Wave Ratio (VSWR), an effective heating process can be performed on the portion to be heated. That is, although differing depending on various conditions, it is considered, in principle, that when the heating process is performed in a state that there is a small amount of reflected wave, effective heating can be performed. As a result, when the frequency of the microwave is changed according to the voltage standing wave ratio, it is considered that the effective process may be enabled. Since such an effective heating process is possible, for example, when performing a process for heating and coagulating a liver of a living body, the coagulation over a wide range can be performed in a short period of time, which is an advantage. It is noted that "to change the microwave" means to change the frequency of the microwave, change the output of the microwave, and so on, for example.

When such a configuration is adopted, it is possible to artificially change the microwave. However, it is preferable to adopt a configuration such that control means for changing the microwave is provided, and based on the received reflected wave, the control means is arranged to control to change the microwave.

In the microwave induction heating device according to the invention of the subject application, it is preferable to have a temperature detecting means for detecting the temperature of the object being a portion to be heated or the microwave oscillation means. With this configuration, based on a temperature detected by the temperature detecting means, the microwave oscillated by the microwave oscillation means can be changed, and according to a change in state of the portion to be heated, the precise heating process can be performed.

When such a configuration is adopted, it is possible to artificially change the microwave. However, it is preferable to adopt a configuration such that control means for changing the microwave oscillated from the microwave oscillation means is provided, and based on the temperature detected by the temperature detecting means, the control means is arranged to control to change the microwave.

In the microwave induction heating device according to the invention of the subject application, it is preferable to adopt a configuration such that an electrode for irradiating the object being a portion to be heated with a microwave in a contact state is provided, and the electrode is arranged to be replaceable, in which according to types of the electrode, the microwave oscillated by the microwave oscillation means can be changed.

With this configuration, according to the object to be heated (according to a diseased site, for example), the electrode can be changed, and also, according to the changed electrode, the frequency of the microwave can be changed. Thus, the precise heating process can be performed.

In the microwave induction heating device according to the invention of the subject application, it is preferable to adopt a configuration such that the microwave oscillation means is arranged to irradiate the heating portion with a microwave continuous in time, and thereby, the effective heating process can be performed.

EXPLANATION OF SYMBOLS

Figure 1:
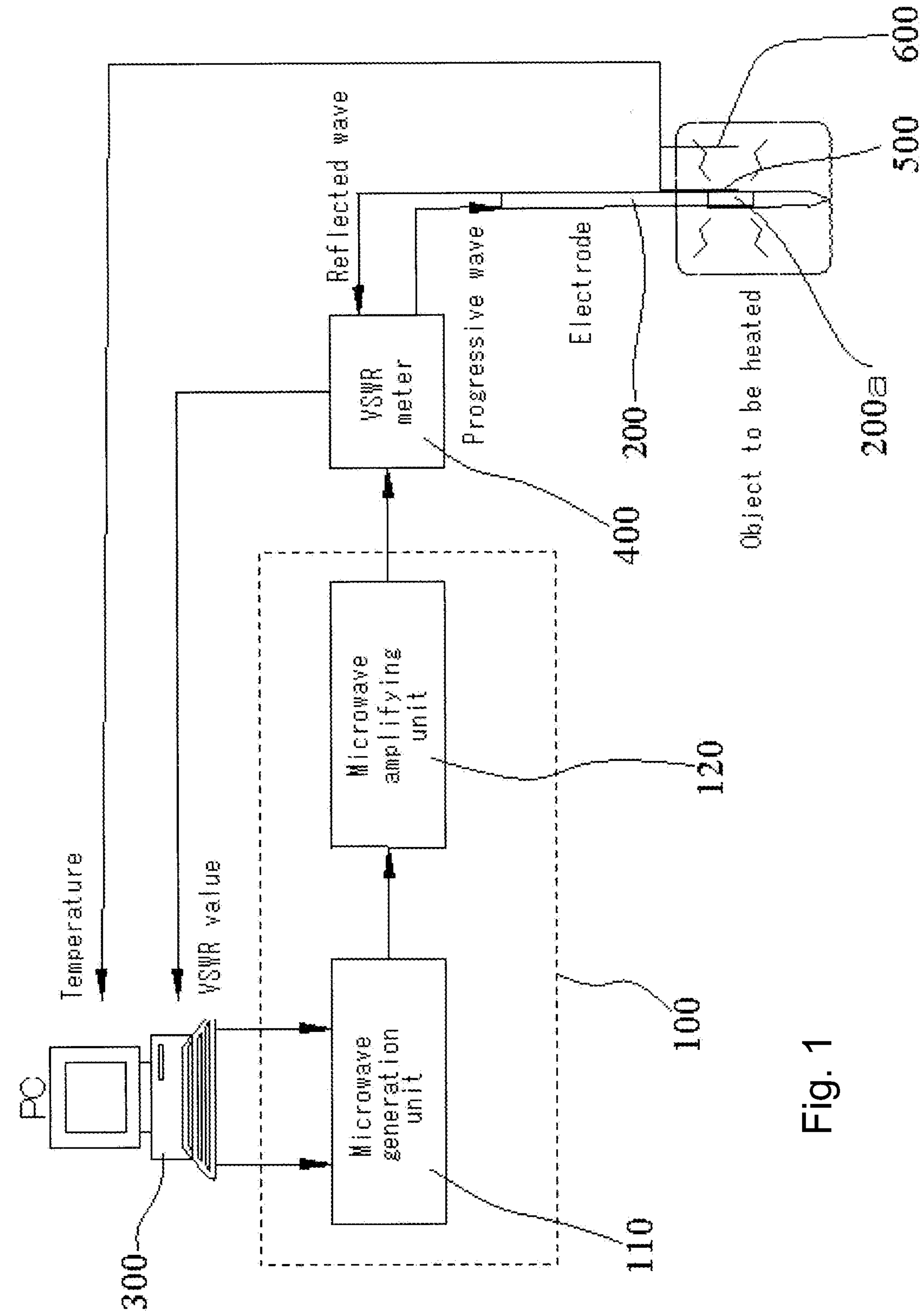
FIG. 1 is an explanatory diagram of a schematic configuration for describing the schematic configuration of a microwave surgical device of an embodiment of the invention of the subject application.

100: Microwave oscillation unit
110: Microwave generation unit
120: Microwave amplifying unit
200: Electrode
200*a*: Microwave irradiating unit
210: Needle-shaped body
220: Contact member
300: Computer
400: Voltage standing wave ratio meter
500: Temperature detecting means
600: Temperature detecting means

BEST MODE FOR CARRYING OUT THE INVENTION

As one embodiment of the invention of the subject application, a microwave surgical device is used as an example, with a description given below.

First, the microwave surgical device of the embodiment is provided with: a microwave oscillation unit 100 made of a microwave generation unit 110 and a microwave amplifying unit 120; an electrode 200 connected to the microwave oscillation unit 100, for irradiating a portion to be heated with a microwave of the microwave oscillation unit 100; and control means 300 for controlling the microwave oscillation unit 100. In the embodiment, the control means 300 is configured by a computer 300.

The electrode 200 is connected to the microwave amplifying unit 120 of the microwave oscillation unit 100 in a manner to be replaceable. Also, in the embodiment, the electrode 200 is connected to the microwave amplifying unit 120 of the microwave oscillation unit 100 via a voltage standing wave ratio meter 400, and the electrode 200 is arranged to receive a reflected wave of the irradiated microwave so as to detect a ratio between a progressive wave and the reflected wave in the voltage standing wave ratio meter 400. The voltage standing wave ratio meter 400 is arranged so as to transmit the detected data to the computer 300.

The overall shape of the electrode 200 substantially is needle-like, and the electrode 200 is configured by a needle-shaped body 210 having a microwave irradiating unit 200*a* on its external surface, temperature detecting means 500 disposed on the external surface of the needle-shaped body 210, and a contact member 220 which is coated on the external surfaces of the needle-shaped body 210 and the temperature detecting means 500 and which is in a contact state with the portion to be heated during a heating process. The microwave irradiating unit 200*a* is positioned terminally with an interval of approximately 10 mm, for example, from the distal end of the needle-shaped electrode 200, and is arranged so as to irradiate the portion to be heated with the microwave. The temperature detecting means 500 is connected to the computer 300, and is arranged so as to transmit the detected data to the computer 300.

Figure 2:
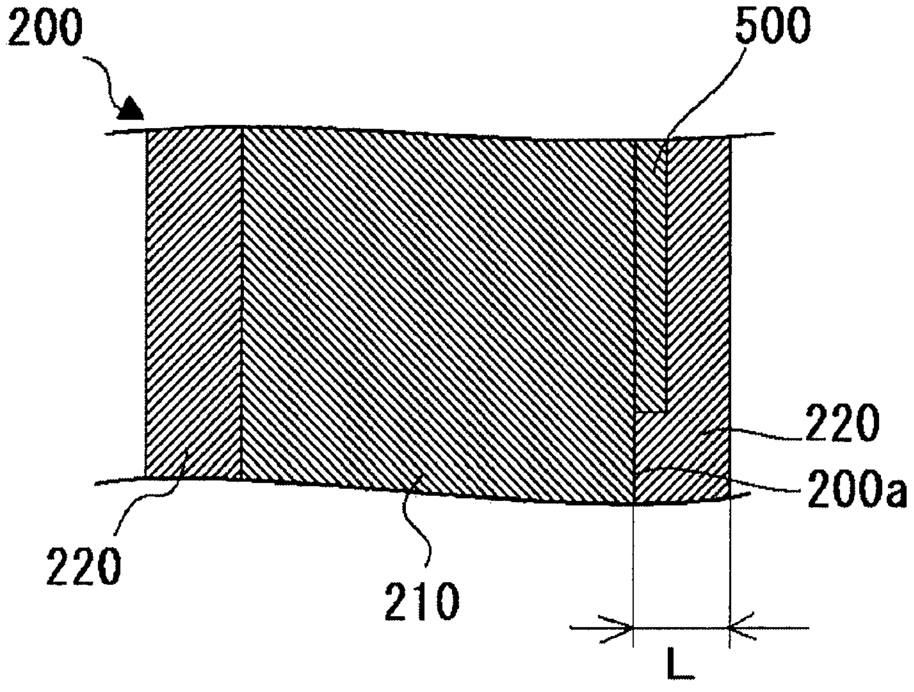
FIG. 2 is a cross-sectional view of enlarged main parts of an electrode used in the embodiment.

In the embodiment, the contact member 220 is made of polyfluorinated ethylene resin such as Teflon (trademark), for example, and is arranged to have a thickness of approximately 0.4 mm (L in FIG. 2). By the contact member 220, a gap of 0.4 mm or more is present between the microwave irradiating unit and the portion to be heated, and thus, a contacted site discoloration, etc., can be precisely prevented. The aforementioned advantage can be exhibited by making the gap between the microwave oscillation unit and the contacted site of the object 0.1 mm or more. Preferably, the gap is 0.2 mm or more, and more preferably, 0.4 mm or more.

In the embodiment, the temperature detecting means 500 is incorporated in the electrode 200, and also second temperature detecting means 600 for detecting the temperature of a position kept apart from the electrode 200 is provided. For the second temperature detecting means 600 for detecting a temperature outside the electrode 200, that having a substantially overall needle-shaped mode can be adopted. In the embodiment, the electrode 200 having the two temperature detecting means 500 and 600 is described, and however, it is possible to change, where appropriate, by design to adopt only either one of the temperature detecting means.

The computer 300 as the control means 300 controls the microwave generation unit 110 of the microwave oscillation unit 100, and is arranged so as to change a frequency/output of the generated microwave. Herein, the computer 300 is arranged so as to change substantially continuously the frequency and the output of the microwave generated in the microwave generation unit 110. It is noted that "substantially continuously" means that the computer 300 is arranged to change from a low frequency/low output to a high frequency/ high output by multiple stages at a predetermined ratio (for example, at a constant ratio). For example, this is meant to include changing a frequency for each 1 MHz.

Also, the microwave generation unit 110 is arranged so that the microwave continuous in time (microwave not intermittent in time (microwave in which a time of 0 output is not continued)) is generated, and is arranged so that the microwave generated in the microwave generation unit 110 is amplified in the microwave amplifying unit 120, and then, transmitted to the electrode 200.

It is possible that the computer 300 is arranged so as to automatically change (automatically control) the frequency of the microwave, etc., based on the data transmitted from the voltage standing wave ratio meter 400 or the temperature detecting means 500 and 600, and also to change (manually control) the frequency of the microwave, etc., by input of an operator. It is further possible that the computer 300 is arranged so as to selectively perform both operations (automatic control/manual control). In addition, the computer 300 is able to change the frequency of the microwave, etc., according to a change of the electrode 200.

Furthermore, as described in greater detail, the computer 300 can be arranged so as to change the frequency of the microwave when determining that a VSWR value detected in the voltage standing wave ratio meter 400 is raised. In doing so, it is considered that an effective heating process operation can be enabled.

The computer 300 can be arranged so as to stop the output of the microwave when determining that the VSWR value detected in the voltage standing wave ratio meter 400 exceeds a constant value. That is, when the VSWR value that exceeds a constant value is detected, it is considered that an abnormality may be generated in the heating operation, and when the output of the microwave is adjusted at this time, the abnormal heating operation can be stopped.

Further, the computer 300 can be arranged so as to change the frequency/output of the microwave when determining that the temperature detected in the temperature detecting means 500 and 600 does not exceed the constant temperature (when determining that the heating is not precisely performed). Thereby, when the heating processing operation is insufficient, if a microwave under a preferable condition is irradiated, the effective heating processing operation can be performed.

The computer 300 can also be arranged so as to adjust the microwave when determining that the temperature detected in the temperature detecting means 500 and 600 exceeds the constant temperature. More specifically, for example, when the temperature detected by the temperature detecting means 500 and 600 reaches the constant temperature or more, the computer 300 can be arranged so as to stop the output of the microwave. That is, for example, when a constant temperature or more is detected in the temperature detecting means 500 incorporated in the electrode 200, if the output of the microwave is adjusted, carbonization of the object to be heated on the periphery of the electrode 200 can be precisely prevented, and also when a constant temperature or more is detected in the second temperature detecting means 600, if the output of the microwave is adjusted, heating/coagulation outside a desired range can be prevented.

It is noted that when the abnormality is detected during a heating processing operation by arranging abnormality-occurrence informing means (for example, an alarm) in the computer 300, the abnormality can be informed to the operator by the abnormality-occurrence informing means, which is a matter changeable by design, where appropriate.

The aforementioned embodiment provides an example in which the electrode 200 is of a needle shape. However, the invention of the subject application is not limited thereto. Various types of electrodes 200 may be adopted. In the embodiment, the mode is described that the control means 300 is configured by the computer 300. However, the invention of the subject application is not limited thereto. For example, it may be possible to change by design, where appropriate, to incorporate of a controller integrally in a main body that incorporates the microwave oscillation unit, for example. Further, in the embodiment, the mode is described that the invention of the subject application is used only for a medical appliance. However, the invention of the subject application can be used for industrial use, e.g., used for heating to promote (or inhibit) reactions such as an organic reaction and an inorganic reaction. More specifically, the invention can be applied to a wide range of fields such as inorganic chemistry, ceramics, organic chemistry, and food chemistry.

Hereinafter, experimental examples using the microwave surgical device of the aforementioned embodiment will be described.

In the experimental example 1, the microwave surgical device of the embodiment and the conventional microwave surgical device were used to carry out an experiment in which a chicken egg white was heated for five minutes so that it would be coagulated. In this case, the egg white was placed in a cylindrical container of which the outer diameter was approximately 40 mm, and the container was immersed in a water tank of which the water temperature was approximately 36° C. In doing so, a temperature condition other than heating from the microwave surgical device was set to be constant.

Figure 3:
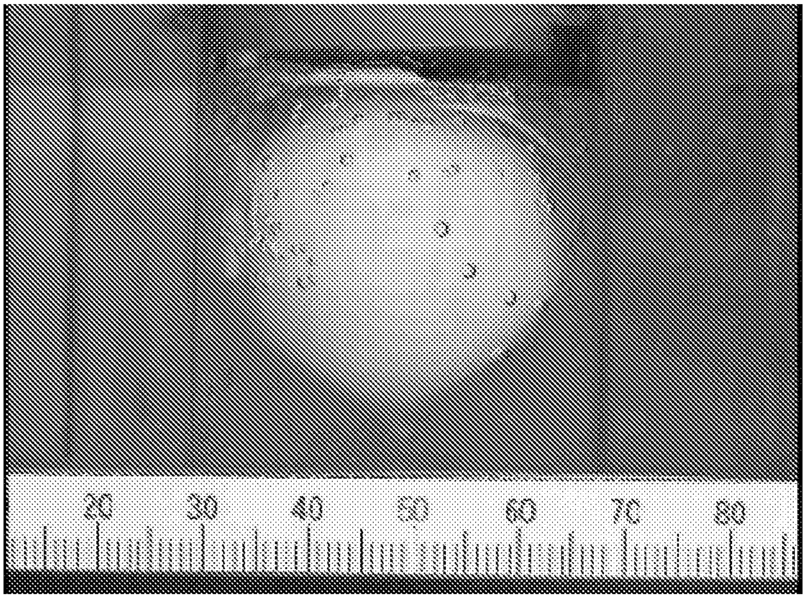
FIG. 3 is a photograph in an experimental example 1, which is obtained after heating and coagulating an egg white by the microwave surgical device of the embodiment, using a first frequency.
Figure 4:
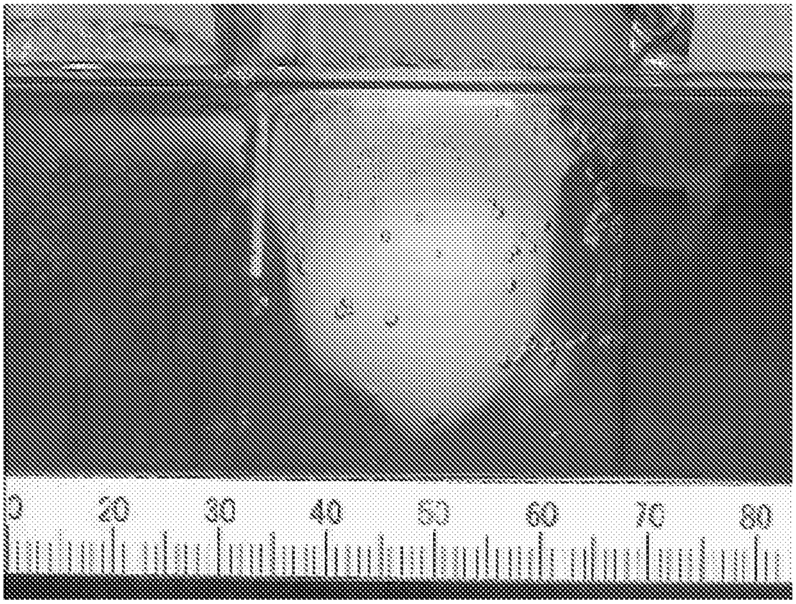
FIG. 4 is a photograph in an experimental example 1, which is obtained after heating and coagulating an egg white by the microwave surgical device of the embodiment, using a second frequency.
Figure 5:
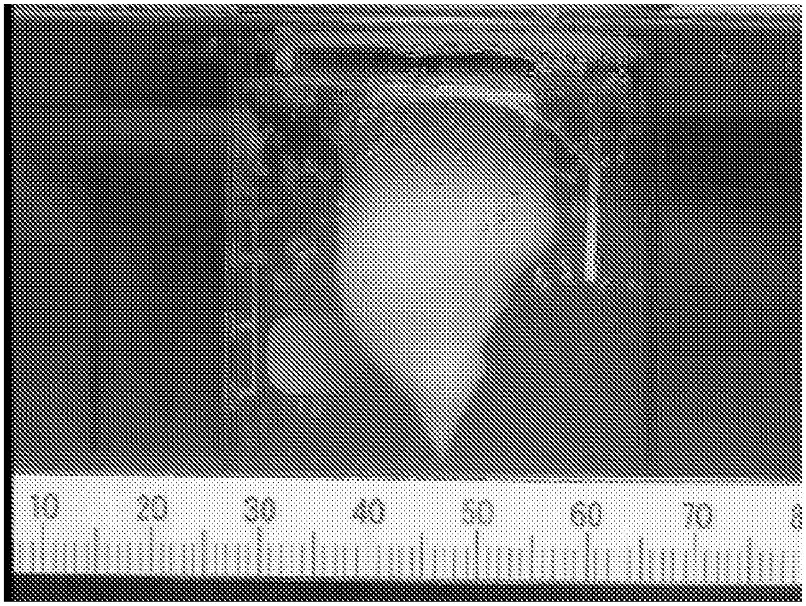
FIG. 5 is a photograph in an experimental example 1, which is obtained after heating and coagulating an egg white by a conventional microwave surgical device.

First, FIG. 3 and FIG. 4 are photographs obtained after the egg white is heated and coagulated by the microwave surgical device of the embodiment. In FIG. 3, a microwave of 2290 MHz and 100 W is irradiated from an electrode, and in FIG. 4, a microwave of 2300 MHz and 100 W is irradiated from an electrode (during the heating process, output/frequency of the microwave was set constant). FIG. 5 is a photograph obtained as a result of irradiating with a microwave by the conventional microwave surgical device (product name "Microtaze," product type "OT-110M," manufactured by Alfresa Pharma Corporation) using a magnetron.

As is obvious from these photographs, the microwave surgical device of the embodiment is able to precisely perform a heating process in a wider range as compared to the conventional microwave surgical device. That is, in the experimental example shown in FIG. 3, the egg white was heated and coagulated in a substantially spherical range of which the diameter was approximately 35 mm. Also, in the experimental example shown in FIG. 4, the egg white was heated and coagulated in a downwardly tapered range in a cylindrical shape of which the average diameter was approximately 30 mm from the upper portion to the lower end. By contrast, in the experimental example shown in FIG. 5, the egg white was heated and coagulated in a range in a cylindrical shape of which the average diameter was approximately 20 mm from the upper portion to the center. At the lower end of the cylindrically shaped range, the coagulation was not found on the right side but deviated only to the left side.

Figure 6:
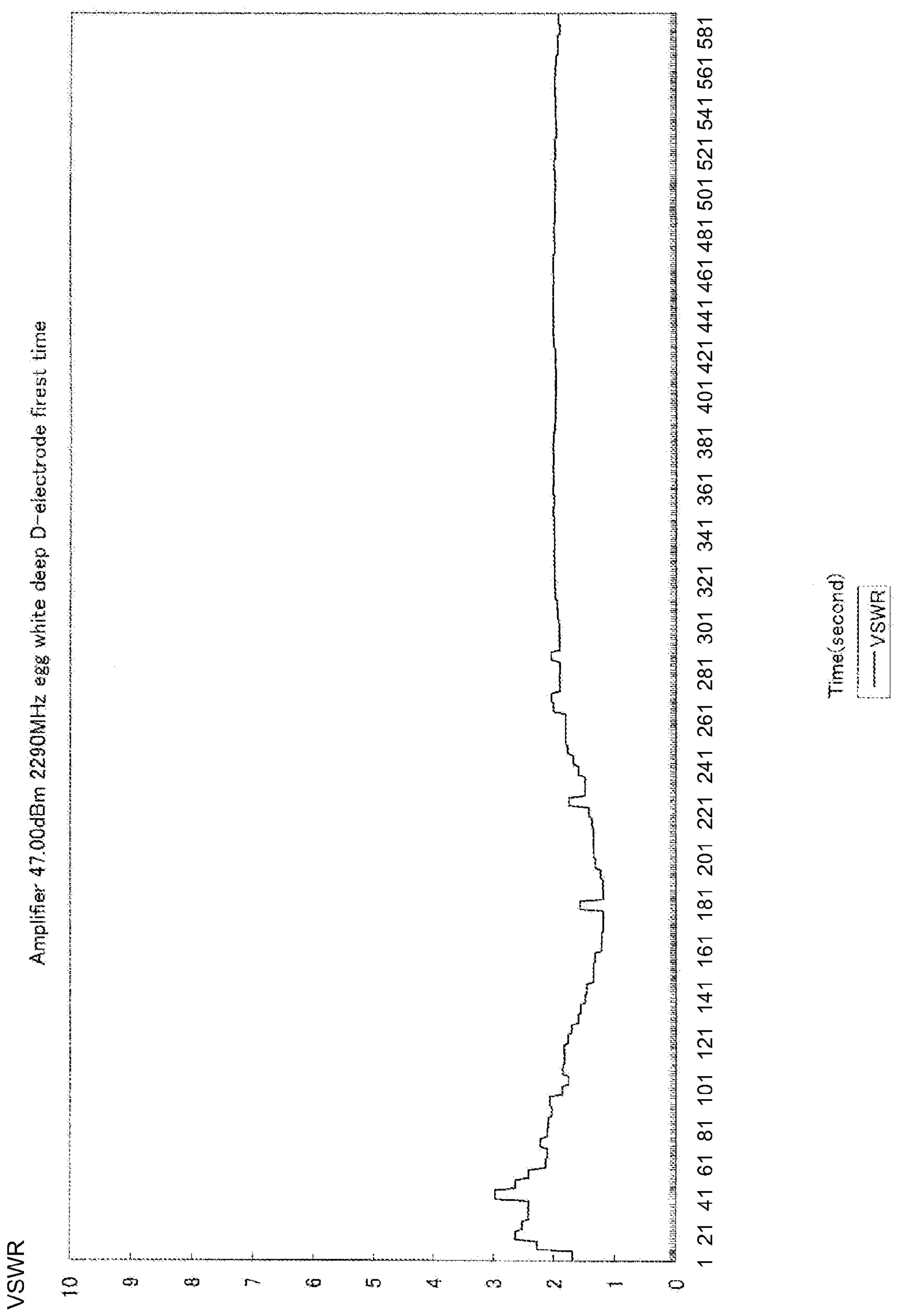
FIG. 6 is a graph in an experimental example 2, for describing elapsed times from a start of an experimental experiment and measurement results of VSWR values, using a first frequency sequence.
Figure 7:
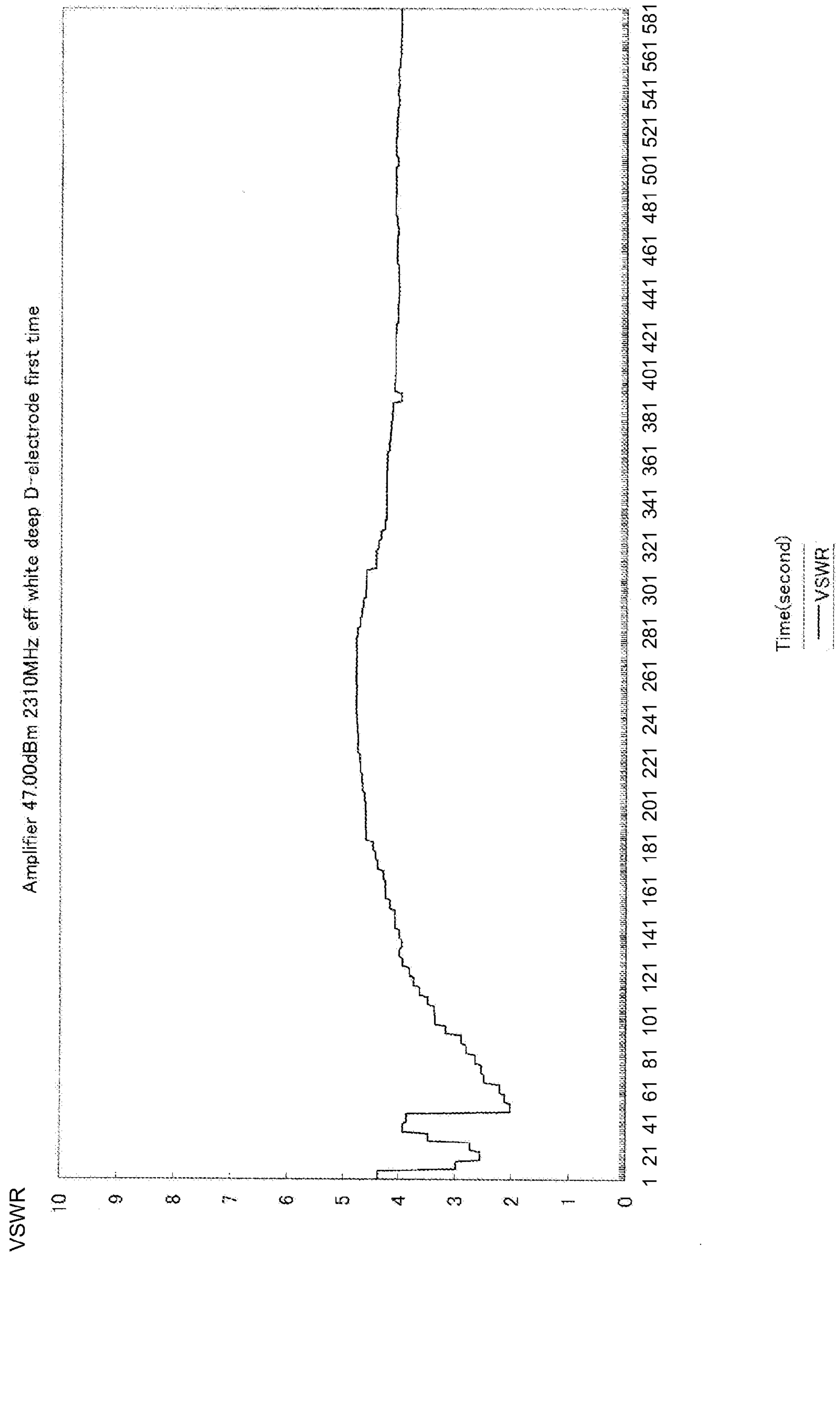
FIG. 7 is a graph in an experimental example 2, for describing elapsed times from a start of an experiment and measurement results of VSWR values, using a second frequency sequence.
Figure 8:
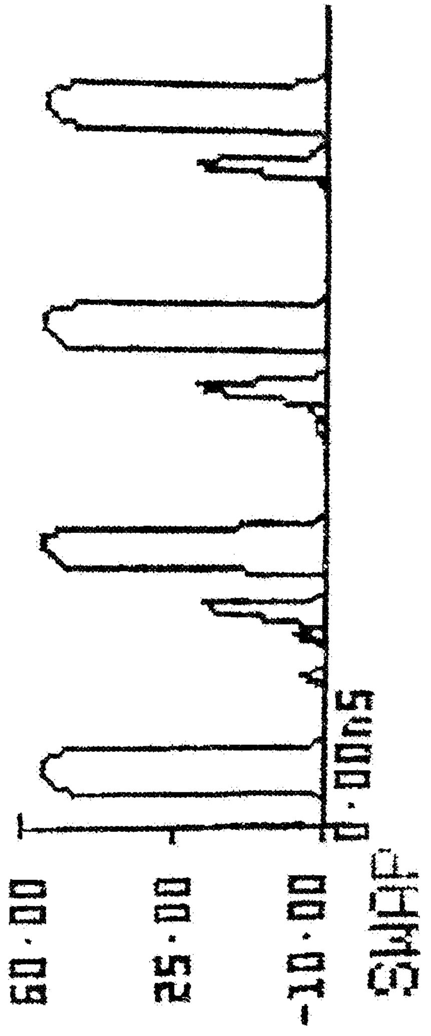
FIG. 8 shows measurement results of output waveforms of a microwave by a conventional magnetron.

In the experimental example 2, the microwave surgical device of the aforementioned embodiment was used to measure a VSWR at the time of heating the egg white for 10 minutes under the condition similar to that of the experimental example 1. In the experimental example 2, when the VSWR was raised, the frequency of the microwave was changed (although the output was constant). In an experiment shown in FIG. 6, a microwave of 2290 MHz and 51.10 W was first irradiated. After an elapse of 30 seconds from the start of the experiment, the frequency was changed to 2310 MHz, and after 90 seconds from the start of the experiment, the frequency was changed to 2313 MHz. In an experiment shown in FIG. 7, a microwave of 2310 MHz and 51.10 W was first irradiated. After an elapse of 30 seconds from the start of the experiment, the frequency was changed to 2295 MHz.

As is seen in this experimental example, while the heating process is performed, a VSWR value is sometimes raised. The rise of the VSWR value is considered to be due to the solidification of the object to be heated, etc. When the VSWR value is raised in this way, the frequency is changed as described above, and thereby, the rise of the VSWR value can be inhibited. Therefore, in this manner, it is considered that an effective heating process can be obtained.

In the experiments, the output was set to 51.10 W, and provided that the output is set high, i.e., approximately 200 W, there is a concern that the problem of the rise of the VSWR value becomes severe. Therefore, when a heating process operation by high output is performed, it is thought that the change in frequency becomes particularly effective.

The invention claimed is:

1. A microwave induction heating device for heating a portion of an object, comprising:

microwave oscillation means for oscillating a microwave to heat the object by microwave induction;

an electrode for irradiating the object with a microwave oscillated from the microwave oscillation means in a contact state with the object;

a first temperature detecting means separate and spaced from the electrode and operable to detect a temperature of the object outside the electrode, the electrode having a microwave irradiating unit for oscillating the microwave, a second temperature detecting means disposed on an external surface of the microwave irradiating unit and a contact member, the contact member being coated on the external surface of the microwave irradiating unit and the second temperature detecting means being operable to contact the object during heating; and the microwave oscillation means being operable to change a frequency of the microwave oscillated by the microwave oscillation means based on temperatures detected by the first and second temperature detecting means.

2. The microwave induction heating device according to claim 1, wherein the microwave oscillation means is operable to change the frequency of the oscillated microwave substantially continuously.

3. The microwave induction heating device according to claim 2, wherein the microwave oscillation means comprises a microwave generation unit for generating a microwave and a microwave amplifying unit for amplifying the microwave generated in the microwave generation unit, and the microwave generation unit is operable to change a frequency of the microwave substantially continuously.

4. The microwave induction heating device according to claim 1, wherein the microwave oscillation means is operable to receive a reflected wave reflected on the object.

5. The microwave induction heating device according to claim 4, wherein the microwave oscillation means is operable to change the microwave oscillated from the microwave oscillation means based on the received reflected wave.

6. The microwave induction heating device according to claim 5, further comprising control means for changing the microwave oscillated from the microwave oscillation means, wherein the control means is operable to change the microwave based on the received reflected wave.

7. The microwave induction heating device according to claim 1, further comprising control means for changing a microwave oscillated from the microwave oscillation means; and the control means being operable to change the microwave based on the temperature detected by the temperature detecting means.

8. The microwave induction heating device according to claim 1, wherein the electrode is replaceable, and according to a type of the electrode, the microwave oscillated by the microwave oscillation means can be changed.

9. The microwave induction heating device according to claim 1, wherein the microwave oscillation means is operable to irradiate the object with a microwave that is continuous in time.

10. The microwave induction heating device according to claim 1, wherein:

the first temperature detecting means is operable to be placed in a position in which a portion of the object being heated is disposed between the electrode and the first temperature detecting means.

* * * * *